United States Patent [19]

Marantz et al.

[11] 3,989,622
[45] Nov. 2, 1976

[54] UREASE IN INSOLUBLE FORM FOR CONVERTING UREA PRESENT IN A LIQUID

[75] Inventors: Laurence B. Marantz, Sherman Oaks; Mario G. Giorgianni, Santa Ana, both of Calif.

[73] Assignee: CCI Life Systems, Inc., Van Nuys, Calif.

[22] Filed: May 21, 1973

[21] Appl. No.: 362,120

Related U.S. Application Data

[63] Continuation-in-part of Ser. No. 102,715, Dec. 30, 1970, abandoned.

[52] U.S. Cl. .................... 210/22 R; 195/DIG. 11; 210/321 B
[51] Int. Cl.[2] .................................... B01D 13/00
[58] Field of Search ............... 195/63, 68, DIG. 11; 210/22, 321

[56] References Cited
UNITED STATES PATENTS

| | | | |
|---|---|---|---|
| 2,717,852 | 9/1955 | Stone | 195/63 X |
| 3,095,307 | 6/1963 | Scott et al. | 195/68 X |
| 3,096,253 | 7/1963 | Koh et al. | 195/63 X |
| 3,382,983 | 5/1968 | Stewart | 210/290 X |
| 3,527,674 | 9/1970 | Deutsch | 195/63 X |
| 3,650,967 | 3/1972 | Johnson | 195/63 |
| 3,666,627 | 5/1972 | Messing | 195/63 X |
| 3,669,841 | 6/1972 | Miller | 195/68 X |
| 3,669,880 | 6/1972 | Marantz et al. | 210/22 |

OTHER PUBLICATIONS

Silman et al., Water Insoluble Derivatives of Enzymes, Antigens and Antibodies, Annual Review of Biochemistry, vol. 35, p. 882, 1966.

*Primary Examiner*—Frank A. Spear, Jr.
*Attorney, Agent, or Firm*—Lyon & Lyon

[57] ABSTRACT

Urease is adsorbed in an aqueous environment on a urease retaining material selected from the group comprising aluminum oxide and magnesium silicate and is thereafter insoluble so that when contacted by liquid containing urea, the urea is converted into ammonium carbonate while the urease remains adsorbed on the retaining material.

43 Claims, 2 Drawing Figures

UREASE IN INSOLUBLE FORM FOR CONVERTING UREA PRESENT IN A LIQUID

This Application is a Continuation-In-Part of patent application Ser. No. 102,715, filed Dec. 30, 1970, entitled COLUMN FOR A CIRCULATING DIALYSATE SYSTEM CONTAINING UREASE IN INSOLUBLE FORM now abandoned.

BACKGROUND OF THE INVENTION

The field of this invention relates to a substance which causes removal of urea from a liquid. This substance can be utilized in combination with an artificial kidney to effect removal of urea from the dialysate solution employed within the artificial kidney prior to the dialysate solution being reconducted through the artificial kidney as one of the various embodiments of the invention.

A common kidney disorder within animals is renal failure. Renal failure is when the kidneys are unable to carry on their normal function of excreting wastes and balancing the internal chemical environment of the body. Renal failure may occur abruptly as due to an obstruction of the urinary tract but most often develops gradually because of progressive destruction of renal tissue by disease. The end result of renal failure is that complete excretion of certain substances within the blood is no longer possible and their blood concentrations therefore rise.

One of the more important substances which it is necessary to remove from the blood is nitrogenous waste such as urea.

Within recent years, it has been common to employ the use of an artificial kidney to partially replace the function of the natural kidney. Primarily, procedures using such artificial kidneys provide for the conducting of blood outside the body and across a semi-permeable membrane system with a saline solution passing on the other side of the membrane. The saline solution used in this procedure is known as "dialysate". The undesirable waste products within the blood are caused to pass through the membrane into the dialysate solution by a process known as dialysis. Normally, such artificial kidneys are employed upon human beings. Hereinafter, the use of such an artificial kidney will be described in relation to the human being although such artificial kidneys may be employed within lower order animals.

Once the dialysate solution has picked up the waste products of the blood, either the dialysate solution must be discarded or the concentration of the waste products must be reduced in the dialysate solution prior to the solution being recirculated through the artificial kidney. The dialysate solution in itself is relatively inexpensive. However, for a particular treatment which usually takes from 8 to 10 hours in time, between 50 and 100 gallons of the dialysate solution will be passed through the artificial kidney. The need for such a large volume of dialysate substantially increases the cost of each treatment, the complexity of required equipment, and the cost of the equipment installation. Therefore, it has been desirable to use only a small volume of the dialysate solution by reducing the concentration of the waste products therefrom and recirculating it back through the artificial kidney.

The most difficult waste material to remove from the dialysate solution is the nitrogenous type of waste material such as urea. A desirable way to effect the removal of urea from a dialysate solution has been described in U.S. Pat. No. 3,669,880 granted June 13, 1972. In this patent, the urea in the dialysate system is converted into ammonia carbonate by urease and the ammonium ion is thereafter picked up and replaced by sodium and hydrogen as the solution flows through zirconium phosphate.

It has been common in the past as taught in U.S. Pat. No. 3,669,880 to intermix the urease with diatomaceous earth (also known as diatomite). This material is defined as a light pliable siliceous material derived chiefly from diatom remains and used especially as a filter. The diatomite is intended to hold the urease within a fixed layer in its column. However, the diatomite does not make the urease completely insoluble in the liquid stream, and in the preferred embodiment described in U.S. Pat. No. 3,669,880 some small amount of urease could dissolve into the liquid and be carried through the column and into other regions of the recirculating system. Wherever the urease lodges it would act to convert the urea in the circulating liquid into ammonium carbonate at that site. In that embodiment this could result in measurable ammonia concentration levels downstream of the column.

SUMMARY OF THE INVENTION

This invention is founded upon the principle that the enzyme urease, upon being brought into contact with certain insoluble materials, in the presence of an aqueous solution, is removed from solution and adsorbed on the insoluble materials, thereby becoming insoluble to water. At the same time the ability of the urease to hydrolyze urea is not impaired. The types of material which are known to adsorb the urease in the presence of an aqueous solution and render it insoluble to water are magnesium silicate and aluminum oxide.

Adorption Adsorption the urease to the urease retaining material occurs only in a liquid environment. There are several techniques to bring the urease and urease retaining material together under such an environment.

One technique is to mix the urease with the urease retaining material both in dry powder form, and to add liquid to this mixture.

Another technique is to mix the urease with the urease retaining material both in dry powder form, to place the material in a container such as a column, and to flow liquid into one end of the column, through the mixed materials and out the other end of the column. In this particular configuration it is obvious that some of the dry granules of urease at the downstream surface of the layer may not be in intimate contact with the particles of urease retaining material at the moment the liquid stream passes through this surface of the layer. Therefore, this urease can be carried downstream before it has had an opportunity to contact a particle of the urease retaining material in order to become adsorbed thereon. Therefore although this configuration may be satisfactory in some embodiments of the invention, in those embodiments in which it is desirable to retain all of the urease within a definite layer within the column it is desirable to add a second layer of urease retaining material alone. The function of the second layer is to provide some particles of urease retaining material in the path of urease which may be carried downstream from the first layer, so that the urease may come into intimate contact with such urease retaining material particles and thereby become adsorbed and insoluble.

The column can be in the form of a separate cartridge which can be incorporated into any type of urea removing system and which can be easily replaced after a selected period of time.

Another embodiment of the invention is placement of the urease retaining material alone in dry powder form in a path of a flowing liquid, and injecting a solution of urease upstream of the layer of urease retaining material. This urease solution may be injected upstream either just prior to initiation of liquid flow, in which case the liquid will assist in carrying the urease solution into the urease retaining material, or just after initiating liquid flow through the urease retaining material. The latter method is preferred since it permits the urease retaining material to become completely wetted prior to contact with the urease, and thus increases the possibility that when the urease contacts the particles of urease retaining material this contact will occur in a liquid environment, thus enabling the urease to become adsorbed to the urease retaining material and to become insoluble in the liquid.

While the present invention is described in connection with its use in a column in an artificial kidney system employing a recirculating dialysate solution, it is obvious that the invention can be used in any system in which it is desirable to remove urea from a liquid. For instance, a treatment technique known as peritoneal dialysis uses a dialysate solution, which is brought into contact with a natural membrane, the peritoneum, by puncturing the abdominal wall. This dialysate is particularly expensive, since it must be sterile. The embodiment shown may be used to regenerate peritoneal dialysate to permit reuse of a small recirculating volume.

Also, in urine recovery systems the invention can be used to remove the urea from urine which is to be converted back into water. The invention can likewise be used in a fertilizer system wherein urea solution is converted into ammonia for use as the fertilizer substance. In this instance the liquid might flow once only through a column as described. Alternately, the liquid could be treated in batch form by pouring it over urease adsorbed on the urease retaining material, allowing it to stand or circulate within a batch container, and then pouring off the solution from which urea has been removed.

The containment of urea removing substance is not limited to a column or a tank. The urease and urease retaining material can be intermixed in a liquid solution and encapsulated within a semi-permeable membrane by encapsulation techniques well known in the art. If the membrane material is permeable to urea, but impermeable to other materials in the liquid which it is desirable to retain, then when the liquid is poured over such capsules urea would be selectively removed.

In addition to this substance being used to remove urea from aqueous solutions, it can be used to remove urea from any liquid in which urea will dissolve and which will not remove or deactivate the adsorbed urease. The invention also encompasses the methods described herein.

In an artificial kidney system described herein as the shown embodiment, the urease is mixed with the urease retaining material, both in dry powder form, forming a first layer within a flow-through container (or column) followed immediately by a second layer of only the urease retaining material, both such layers being placed upstream of a layer of zirconium phosphate or other ammonia sorbent. As described in U.S. Pat. No. 3,669,880 the zirconium phosphate picks up the ammonium ion so that the ammonia concentration in the outflow stream may be caused to be zero. While this is useful in the shown embodiment the pick up of ammonium ions from the fluid stream is not essential to the invention. As fluid flow is initiated through this column, upon initial wetting of the first layer the urease become adsorbed in insoluble form on the urease retaining material. The small amount of urease at the downstream surface of this layer which may not be in intimate contact with particles of the urease retaining material at the moment the fluid flow reaches that point will be carried into the next layer consisting only of urease retaining material and upon contact with a particle in this layer will become adsorbed and insoluble.

DETAILED DESCRIPTION OF THE SHOWN EMBODIMENT

Figure 1:
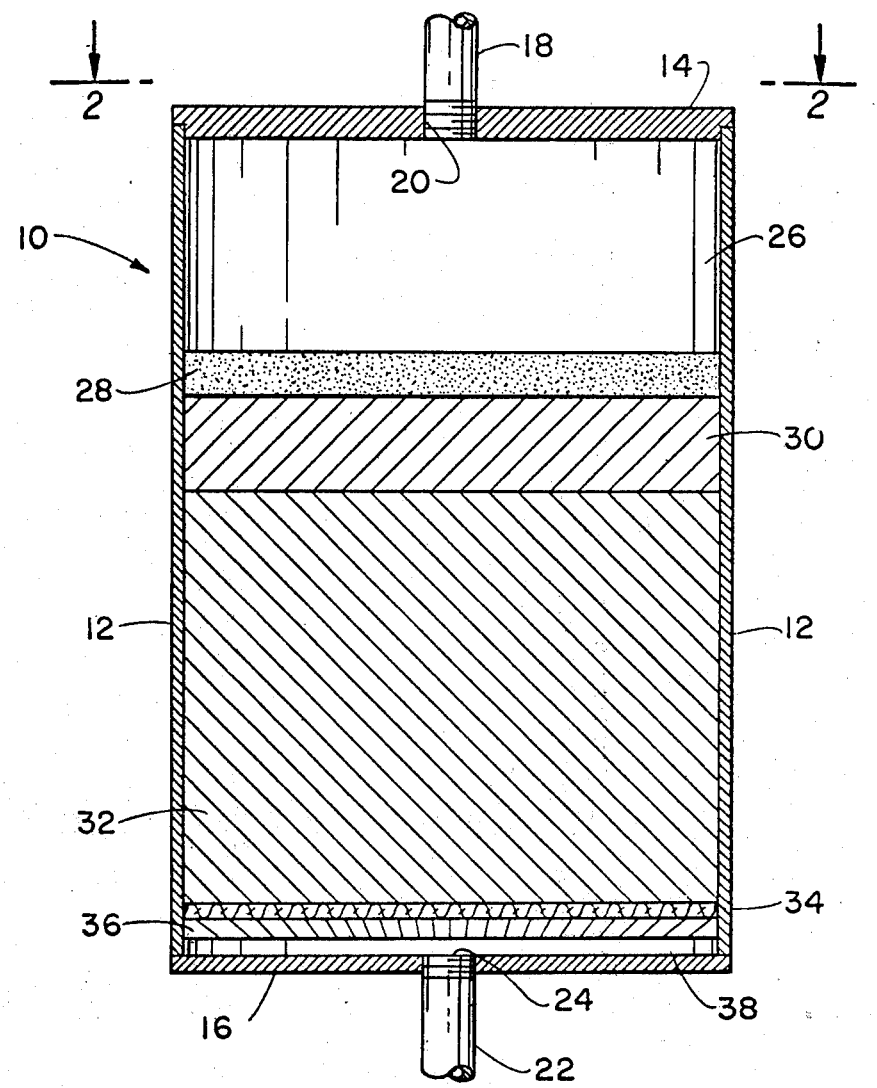
FIG. 1 is a cross-sectional vertical section of a column for the treatment of dialysate solution incorporating this invention.
Figure 2:
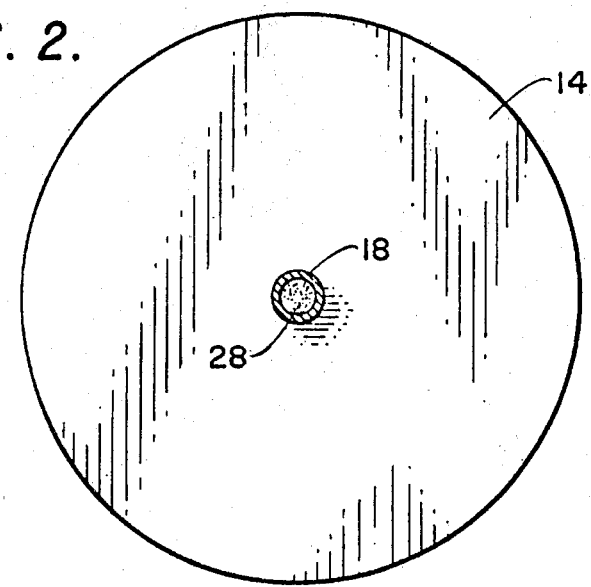
FIG. 2 is a plan view of the column of FIG. 1 taken along line 2—2 of FIG. 1.

The embodiment of the invention chosen for purposes of illustration comprises a column 10 constructed in the shape of a container having a circular side wall 12 closed at one end by wall 14 and closed at the opposite end by wall 16. The column is to be located at any of various positions within a recirculating dialysate system. The particular location of the column 10 is to be a matter of choice or design. The dialysate enters the column 10 from passage 18 which connects with opening 20 within the end wall 14. The dialysate is to exit from the column 10 through passage 22 which connects with opening 24 located in the end wall 16. A primary purpose of the column 10 is to remove the urea from the dialysate solution so that the same solution can be recirculated continuously through the artificial kidney to adsorb urea from the blood of the patient.

The column 10 contains an open space 26 adjacent the end 14. The function of the open space 26 is to receive the dialysate entering from passage 18 and serves to disperse the solution over the area of the column. The open space 26 terminates into a first layer 28 of material. Layer 28 in the shown embodiment initially comprises a dry powder consisting of a mixture of finely divided urease and a urease retaining material from the group consisting of magnesium silicate and aluminum oxide. Each one of the materials of the group could be employed singularly or in combination thereof. However, normally a single material of the group would be employed and urease added thereto.

In use in a dialysate system, the dialysate stream enters from passage 18 through opening 20 into an open space 26 and through layer 28. As the urease and urease retaining material are wetted, the urease is then adsorbed on the urease retaining material. As a result, the urease becomes insoluble to water, the primary component of the dialysate solution, therefore rendering it impossible for the urease to become soluble within the dialysate solution. However, the ability of the urease to hydrolyze urea is not impaired.

Located immediately below the first layer 28 is the second layer 30. The second layer 30 is comprised of one or a mixture of the urease retaining materials of the above referred to group and not intermixed with the urease. In the event that any granules of urease which are located on the downstream surface of layer 28 are not in intimate contact with a particle of the urease retaining material at the moment the dialysate solution contacts the urease, these granules will be carried beyond layer 28. In such case, this urease will be brought in contact with particles of urease retaining material in layer 30, and this urease will be adsorbed upon these particles of the above referred to group. If the second layer 30 is not employed this urease would then pass on through the column.

In proper operation, neither urease nor urea is found in the solution which has passed through layers 28 and 30. The insolubility of the urease on aluminum oxide or magnesium silicate is independent of temperature between 0° and 50° C. Below 0° C the solution freezes, and above 50° C the urease becomes inactive. The insolubility of urease is also independent of the state of the urease as it is added to the layer material, or the rate of introduction to the layer of material. Since urease alone is soluble in aqueous solutions, pure urease granules would dissolve if used for the conversion of urea contained in an aqueous solution. However, the urease becomes insoluble in these liquid solutions adsorbed on the urease retaining material.

In this shown embodiment of the invention in an artificial kidney system, it is also desirable to remove from the fluid stream the ammonium carbonate which results from the conversion of urea by the urease. This may be accomplished by the use of zirconium phosphate ion exchange in fine particle form, shown as a third layer 32 located adjacent the second layer 30. A filter 34 is located between the zirconium phosphate layer 32 and the flow director device 36, to retain the powdered material. The function of the flow director device 36 is to direct the dialysate flow to outlet opening 24 within the bottom wall 16. A space 38 exists between the flow director 36 and the opening 24 to permit the flow of dialysate solution to the passage 22.

The solution entering the column 10 from passage 18 is the standard dialysate solution plus the waste products (impurities) picked up from the patient by the artificial kidney (not shown). One of the major impurities is urea.

As the dialysate solution passes through the layer 28 in column 10, the urea is converted into ammonium carbonate in accordance with the following relationship:

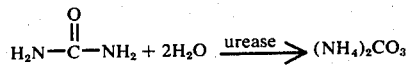

In a particular embodiment of the invention, such as the shown embodiment described, if an adequate amount of urease is provided, and if the urease layer is thick enough relative to the fluid flow rate to allow sufficient time for all of the urea to be converted to ammonium carbonate, then all of the urea is converted by the time the solution enters the zirconium phosphate layer 32. For instance, the incoming solution is passage 18 can contain 20 milligrams blood urea nitrogen per 100 cc of solution and may be caused to drop to 0 milligrams as it enters the zirconium phosphate 32. After leaving the urease, there will be no further change in the urea concentration. As described in U.S. Pat. No. 3,669,880, the zirconium phosphate picks up the ammonium ion so that the ammonium concentration in the outlet line 22 may be caused to be zero or substantially zero as desired, depending only on the amount of zirconium phosphate utilized and the physical dimensions of the column relative to the dialysate flow rate.

The column described for a circulating dialysate system retains urease insoluble to water in one end of the column and upstream from a sorbent material such as zirconium phosphate. The urease is rendered insoluble by being first mixed in dry powder form with the urease retaining material also in dry powder form, and being placed in a layer so that the dialysate solution disperses through the layer wetting the materials. The liquid environment causes urease in intimate contact with particles of the urease retaining material to become adsorbed thereon, thereby becoming insoluble to water. By confining the urease to the upstream portion of the column, all conversion of urea to ammonium carbonate occurs within a fixed region.

It is apparent that if a urease solution were injected into passage 18 it would flow through opening 20 into open space 26 and intermix with layer 28. In this case layer 28 could initially be only urease retaining material, identical to layer 30. The urease being in solution would provide the aqueous environment to allow the urease to adsorb to the urease retaining material. In addition, as dialysate is introduced into the column any urease which has not penetrated into layers 28 and 30 will go into solution in the dailysate, and would then be carried further downstream where it would become adsorbed upon the urease retaining material.

It is to be noted that some types of commercially available oxide have been found to be more satisfactory than others for this shown embodiment. The reasons why one type of aluminum oxide will adsorb more urease per unit weight than another type appear to relate to the particular method of preparing the aluminum oxide. While some grades of aluminum oxides are less satisfactory for the shown embodiment, this does not mean that the material is inoperative since if sufficient amount of material or a finer form of material or both is used, satisfactory adsorption of urease can be obtained.

In order to obtain an indication of the degree of effectiveness of the urease retaining materials in the preferred embodiment, an aqueous solution of urease was passed through a number of fixed weight samples of alumina (aluminum oxide) and magnesium silicate of mesh sizes desirable for the preferred embodiment, and the excess urease was washed out. A ureas solution of an average concentration of urea applicable to the preferred embodiment was then passed through the same test sample and the percent of urea converted into ammonium carbonate was measured. The higher the conversion, the more urease in insoluble, active form was adsorbed per unit weight on the alumina or magnesium silicate. The results of these tests shown that the calcined and activated alumina such as produced by Aluminum Company of America (Alcoa), Reynolds Metals, or Kaiser hold more urease in active form per unit weight than similar quantities of tabular or hydrated alumina manufactured by one or more of the same companies. Thus, the hydrated and tabular forms are not as satisfactory as the calcined or activated forms of alumina in the shown embodiment.

The test showed that the more tabular and hydrated alumina used at the same mesh size, the greater the conversion of urea into ammonium carbonate. Furthermore, tests with different mesh ranges of tabular and hydrated alumina showed that the finer the mesh size of the alumina, the greater the conversion of urea into ammonium carbonate. In some mesh sizes, five times the amount of tabular or hydrated alumina were required to obtain the same percentage conversion of urea into ammonium carbonate as obtained from a unit amount of activated or calcined alumina. Tabular and hydrated alumina can be ground very fine so that the conversion of urea to ammonium carbonate would be very high but the pressure drop characteristics of the material for a given liquid flow rate would not be as satisfactory for the shown embodiment as that for calcined or activated alumina. A typical mesh size of calcined alumina for use in the embodiment falls within the range of 100 to 325 American Standard mesh. Alcoa utilizes the following designation for alumina: A Grade for calcined; C Grade for hydrated; and T Grade for tabular. Reynolds Aluminum uses RC numbers for calcined and RA numbers for activated alumina and Kaiser Aluminum uses KC numbers for calcined. All of these alumina oxides are operable in the present invention.

It should be noted that these tests were intentionally run with an amount of urease insufficient in even the best case to convert 100% of the urea, in order to have a scale of comparison between different amounts and different types of alumina. In the actual embodiment the amount of alumina utilized is designed to convert all of the urea into ammonium carbonate under conditions of the specific application of this embodiment.

The tests of magnesium silicate show that activated magnesium silicate, such as Woelm Activity 1 produced by M. Woelm Company of Eschwege, West Germany, is more satisfactory in adsorbing urease than talc. Talc is a naturally occurring mined form of magnesium silicate usually found intermixed with other natural contaminants. While finely powdered talc is very efficient in adsorbing urease, the pressure drop characteristics of this form of finely powdered magnesium silicate for a given liquid flow rate is not as acceptable in the preferred embodiment, but may be preferable in other embodiments of the invention described above.

It is possible, however, to select an amount and particle size of magnesium silicate talc so that flow rate ratio to pressure drop is acceptable for a particular embodiment of this invention. Magnesium silicates, in general, all adsorb urease, although their structure and formulas vary. For instance, the magnesium silicate tested had a formula of $Mg_2 Si_3 O_8 \cdot 5H_2O$ (also known as magnesium trisilicate) and the talc tested was $Mg_3 Si_4 O_{11} \cdot H_2O$. For purposes of definition, both talc (natural magnesium silicate) and refined magnesium silicate are considered to be broadly defined as magnesium silicate. A magnesium silicate designated as Biorad M-1 marketed by Bio-Rad Laboratories of Richmond, California, also tested satisfactorily in urea conversion.

What is claimed is:

1. A substance for converting dissolved urea present in a liquid;
   means for locating said substance in said liquid;
   said substance comprising a urease retaining material having urease adsorbed thereon for converting urea in said liquid into ammonium carbonate;
   said adsorbed urease being insoluble in said liquid so that it is not dissolved in the liquid contacting said substance and retaining its ability to convert dissolved urea into ammonium carbonate; and
   said urease retaining material being selected from the group consisting of aluminum oxide and magnesium silicate.

2. The combination of claim 1 wherein said substance is initially a mixture of dry granules of urease and said urease retaining material; and
   said adsorption of urease on said retaining material resulting from contact of said granules with said liquid.

3. The combination of claim 1 wherein said urease retaining material is initially in dry granular form, said urease being adsorbed on said material granules from a liquid solution of urease.

4. The combination of claim 1 wherein said liquid contains water.

5. A combination of claim 1 wherein said liquid is dialysate solution containing urea picked up from a patient and being substantially all water.

6. The combination of claim 5, wherein said dialysate solution is a hemodialysate solution.

7. The combination of claim 5, wherein said dialysate solution is a peritoneal dialysate solution.

8. A substance for converting dissolved urea present in a liquid;
   means for locating said substance in said liquid;
   said substance comprising a urease retaining material having urease adsorbed thereon for converting urea in said liquid into ammonium carbonate;
   said adsorbed urease being insoluble in said liquid so that it is not dissolved in the liquid contacting said substance and retaining its ability to convert dissolved urea into ammonium carbonate; and
   said material consisting of aluminum oxide.

9. A substance for converting dissolved urea present in a liquid;
   means for locating said substance in said liquid;
   said substance comprising a urease retaining material having urease absorbed thereon for converting urea in said liquid into ammonium carbonate;
   said adsorbed urease being insoluble in said liquid so that it is not dissolved in the liquid contacting said substance and retaining its ability to convert dissolved urea into ammonium carbonate; and
   said material consisting of magnesium silicate.

10. A container containing a substance for converting dissolved urea present in a liquid;
    said container being penetratable by said liquid to permit said liquid to contact said subtance in said container;
    said substance comprising a urease retaining material having urease adsorbed thereon for converting urea in said liquid into ammonium carbonate;
    said adsorbed urease being insoluble in said liquid so that it is not dissolved in the liquid contacting said substance and retaining its ability to convert dissolved urea into ammonium carbonate; and
    said urease retaining material being selected from the group consisting of aluminum oxide and magnesium silicate.

11. The combination of claim 10 wherein said liquid contains water.

12. The combination of claim 10 wherein said liquid is dialysate solution containing urea picked up from a patient and being substantially all water.

13. The combination of claim 12, wherein said dialysate solution is a hemodialysate solution.

14. The combination of claim 12, wherein said dialysate solution is a peritoneal dialysate solution.

15. A container as defined in claim 10 having first opening means for introducing liquid into said container; and second opening means for discharging said liquid from said container after conversion of urea in said liquid to ammonium carbonate by the adsorbed urease.

16. A container as defined in claim 15 wherein said substance is permeable to said liquid and is located between said first and second opening means so that said liquid flows through said substance.

17. The combination of claim 16 having urease retaining material located between said substance and said second opening means for adsorbing urease not adsorbed on the urease retaining material comprising said substance.

18. The combination of claim 16 wherein said liquid is circulating dialysate solution returning from an artificial kidney and entering said first passage means.

19. The combination of claim 18 having an ammonium ion sorbent material located between said substance and said second opening means, so that the dialysate solution flows from said substance into said sorbent material.

20. The combination of claim 16 wherein said substance is maintained in said container in layer form located between said two opening means and in the flow path of said liquid.

21. The combination of claim 20 having a second layer of urease retaining material located between said substance layer and said second opening means to absorb any urease leaving said substance layer.

22. A container containing a substance for converting dissolved urea present in a liquid;

said container being penetratable by said liquid to permit said liquid to contact said substance in said container;

said substance comprising a urease retaining material having urease adsorbed thereon for converting urea in said liquid into ammonium carbonate;

said adsorbed urease being insoluble in said liquid so that it is not dissolved in the liquid contacting said substance and retaining its ability to convert dissolved urea into ammonium carbonate; and said material consisting of aluminum oxide.

23. A container containing a substance for converting dissolved urea present in a liquid;

said container being penetratable by said liquid to permit said liquid to contact said substance in said container;

said substance comprising a urease retaining material having urease adsorbed thereon for converting urea in said liquid into ammonium carbonate;

said adsorbed urease being insoluble in said liquid so that it is not dissolved in the liquid contacting said substance and retaining its ability to convert dissolved urea into ammonium carbonate; and said material consisting of magnesium silicate.

24. The method of converting urea dissolved in a liquid to ammonium carbonate comprising the step of contacting said liquid with a substance comprising urease retaining material having urease adsorbed thereon, said adsorbed urease being insoluble in said liquid so that it is not dissolved in the liquid contacting said substance and retaining its ability to convert dissolved urea into ammonium carbonate; and said material being selected from the group consisting of aluminum oxide and magnesium silicate.

25. The method of claim 24 further comprising the steps of, before said contacting step;

supporting said urease retaining material in a supporting means; and adsorbing urease on said urease retaining material.

26. The method of claim 25 including the further step of, prior to said adsorbing step, mixing said urease retaining material and said urease together as dry powders.

27. The method of claim 25, wherein said step of adsorbing urease on said urease retaining material occurs in the presence of a dialysate solution.

28. The method of claim 25, wherein the step of adsorbing urease on said urease retaining material occurs in the presence of a saline solution.

29. The method of claim 25 including the further step of, after said supporting step, adding urease in liquid form to said urease retaining material.

30. The method of claim 29, wherein said urease in liquid form is urease dissolved in a dialysate solution.

31. The method of claim 29, wherein said urease in liquid form is urease dissolved in a saline solution.

32. The method of converting urea dissolved in a dialysate solution to ammonium carbonate comprising the step of contacting said solution with a substance comprising urease retaining material having urease adsorbed thereon, said adsorbed urease being insoluble in said liquid so that it is not dissolved in the liquid contacting said substance and retaining its ability to convert dissolved urea into ammonium carbonate; and said material being selected from the group consisting of aluminum oxide and magnesium silicate.

33. The method of claim 32, wherein said dialysate solution is a hemodialysate solution.

34. The method of claim 32, wherein said dialysate solution is a peritoneal dialysate solution.

35. The method of claim 32 further comprising the steps of, before said contacting step;

supporting said urease retaining material in a supporting means; and adsorbing urease on said urease retaining material.

36. The method of claim 35 including the further step of, prior to said adsorbing step, mixing said urease retaining material and said urease together as dry powders.

37. The method of claim 35 including the further step of, after said supporting step, adding urease in liquid form to said urease retaining material.

38. The method of claim 35, wherein said step of adsorbing urease on said urease retaining material occurs in the presence of a dialysate solution.

39. The method of claim 35, wherein said step of adsorbing urease on said urease retaining material occurs in the presence of a saline solution.

40. A cartridge for converting urea dissolved in a liquid comprising a container;

a mixture located within said container of a urease retaining material and urease both in dry granular form, and opening means in said container for permitting introduction of said liquid into a mixture to produce adsorption of said urease on said urease retaining material, said adsorbed urease being insoluble in said liquid so that it is not dissolved in the liquid contacting said substance and retaining its ability to convert dissolved urea into ammonium carbonate; and said urease retaining material being selected from the group consisting of aluminum oxide and magnesium silicate.

41. A cartridge as defined in claim 40 wherein said container is a column, said opening means being located on one side of said mixture, and a liquid outlet in said container located on the opposite side of said mixture.

42. A cartridge for converting urea dissolved in a liquid comprising a container;

a mixture located within said container of a urease retaining material and urease both in dry granular form, and opening means in said container for permitting introduction of said liquid into a mixture to produce adsorption of said urease on said urease retaining material, said adsorbed urease being insoluble in said liquid so that it is not dissolved in the liquid contacting said substance and retaining its ability to convert dissolved urea into ammonium carbonate; and said urease retaining material consisting of aluminum oxide.

43. A cartridge for converting urea dissolved in a liquid comprising:

a container;

a mixture located within said container of a urease retaining material and urease both in dry granular form, and opening means in said container for permitting introduction of a liquid into said mixture to produce adsorption of urease on said urease retaining material, said adsorbed urease being insoluble in said liquid so that it is not dissolved in the liquid contacting said substance and retaining its ability to convert dissolved urea into ammonium carbonate; and said urease retaining material consisting of magnesium silicate.

* * * * *